US006727396B2

(12) United States Patent
Gartside

(10) Patent No.: US 6,727,396 B2
(45) Date of Patent: Apr. 27, 2004

(54) PROCESS FOR THE PRODUCTION OF LINEAR ALPHA OLEFINS AND ETHYLENE

(75) Inventor: Robert J. Gartside, Summit, NJ (US)

(73) Assignee: ABB Lummus Global, Inc., Bloomfield, NJ (US)

( * ) Notice: Subject to any disclaimer, the term of this patent is extended or adjusted under 35 U.S.C. 154(b) by 94 days.

(21) Appl. No.: 10/055,126

(22) Filed: Jan. 23, 2002

(65) Prior Publication Data

US 2002/0183572 A1 Dec. 5, 2002

Related U.S. Application Data

(60) Provisional application No. 60/263,924, filed on Jan. 25, 2001.

(51) Int. Cl.$^7$ .................................................. C07C 6/04
(52) U.S. Cl. ........................ 585/324; 585/643; 585/644; 585/646; 585/647
(58) Field of Search ................................ 585/324, 643, 585/644, 646, 647

(56) References Cited

U.S. PATENT DOCUMENTS

| 3,485,891 A | * | 12/1969 | Heckelsberg | ................ 585/315 |
| 3,776,974 A | | 12/1973 | Gautier et al. | ......... 260/68.3 D |
| 4,368,345 A | | 1/1983 | Dickinson | .................... 585/643 |
| 4,522,936 A | * | 6/1985 | Kukes et al. | ................ 502/249 |
| 4,709,115 A | * | 11/1987 | Jung et al. | .................. 585/643 |

FOREIGN PATENT DOCUMENTS

GB          1471151        4/1977

\* cited by examiner

*Primary Examiner*—Thuan D. Dang
(74) *Attorney, Agent, or Firm*—Elliot M. Olstein; Raymond J. Lillie

(57) ABSTRACT

Ethylene and hexene-1 are produced from butene-1 by metathesis of butene-1 and isomerization of the hexene-3 produced therein to hexene-1. The initial starting material is a mixed butene stream wherein butene-1 is isomerized to butene-2 with isobutylene being separated therefrom, followed by isomerization of butene-2 to butene-1, with the butene-1 being the feed to the metathesis.

32 Claims, No Drawings

PROCESS FOR THE PRODUCTION OF LINEAR ALPHA OLEFINS AND ETHYLENE

This application claims priority based on, and is a continuation-in-part of, application Ser. No. 60/263,924, filed Jan. 25, 2001, the contents of which are incorporated herein by reference in their entirety.

This invention relates to the production of linear alpha olefins. More particularly, this invention relates to the production of linear alpha olefins having a higher carbon number from alpha olefins having a lower carbon number. More particularly, this invention relates to the production of ethylene and hexene-1.

Linear alpha olefins currently are produced by the selective oligomerization of ethylene. In general, the oligomerization is conducted in the presence of a catalyst, such as an alkylated metal catalyst. Long residence times are used to produce hydrocarbon chains of varying lengths. The olefin double bond remains at the alpha position as each ethylene molecule is added. Ethylene oligomerization produces a wide spectrum of linear alpha olefin products. Extensive fractionation is required to separate the alpha olefins having different carbon numbers.

In accordance with an aspect of the present invention, a linear alpha-olefin having a first number of carbon atoms is subjected to a metathesis reaction under conditions and in the presence of a catalyst that minimizes or eliminates skeletal and/or double bond isomerization to produce a reaction product that includes ethylene and a linear internal olefin (LIO) that has a number of carbon atoms greater than the first number of carbon atoms. Specifically, the feed linear alpha olefin with carbon number is metathesized to ethylene and linear internal olefin with carbon number 2n−2. The resulting linear internal olefin may then be isomerized to produce a linear alpha olefin.

In accordance with an aspect of the present invention, butene-1 is subjected to a metathesis reaction under conditions and in the presence of a metathesis catalyst that minimizes or eliminates skeletal and double bond isomerization to produce a reaction product that includes ethylene and hexene-3. The hexene-3 is then isomerized to hexene-1.

In the metathesis reaction, the catalyst and reaction conditions are such as to minimize isomerization of the butene-1 starting material.

The catalyst used in this aspect for the metathesis reaction may be a supported or unsupported catalyst and the overall catalyst is one that has a minimized amount of both acidic and basic sites.

A catalyst that has a reduced amount of both acidic and basic sites (preferably essentially no acidic and basic sites) improves the selectivity of the metathesis of the lower carbon number alpha-olefin (1-butene) with itself to form ethylene and a linear internal olefin of higher carbon number (3-hexene) by minimizing isomerization.

Metathesis reactions can be characterized as either fully productive, half productive, or non-productive depending upon the symmetry of the molecule with respect to the double bond. Two dissimilar olefins will react in a "fully productive" manner. An example is the reaction of 1-butene with 2-butene. The double bond is in a different position in the respective molecule and these will react rapidly with one another. Two identical molecules will react in either a half productive or non-productive manner. If for example 1-butene reacts with itself, because the double bond is in the same position within each molecule, it will react at a rate considerably slower than the rate of fully productive reactions. If the feed molecules are identical and symmetric around the double bond (for example 2-butene reacting with itself), then no reaction will occur and the system is defined as non-productive.

In many metathesis reaction systems, isomerization activity is incorporated to increase the rates of reaction. By allowing for a shifting double bond, half or non-productive reactions can be reduced. Typical isomerization catalysts include basic metal oxides or promoted zeolites.

In one preferred embodiment, the catalyst or catalyst mixture contains essentially no magnesium oxide in that magnesium oxide catalyst promotes isomerization. Thus, for example, a preferred catalyst (supported or not supported) is a Group VI B or Group VII B metal oxide such as tungsten oxide, molybdenum oxide, or rhenium oxide, with tungsten oxide being particularly preferred.

If a support is used, such support has a minimized amount of both acidic and basic sites and preferably essentially no acid and essentially no basic sites. Preferred supports are silica or zirconia oxide.

Although the catalyst may include a promoter to reduce acidity; for example, an alkali metal (sodium, potassium or lithium), cesium, a rare earth, etc., in a preferred embodiment, the catalyst does not include a promoter.

Generally reaction conditions that tend to favor the primary reaction and discourage subsequent reactions are preferred. Thus a lower pressure and shorter residence times tend to minimize the isomerization reaction.

In accordance with the present invention, a linear alpha olefin with carbon number n, such as butene-1, is subjected to auto-metathesis with itself (half productive reaction) in the presence of a catalyst and under conditions that minimize isomerization of the linear olefin to produce a reaction product that includes ethylene and a linear alpha olefin of carbon number 2n−2, such as hexene-3. The reaction is:

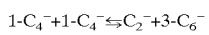

$$1\text{-}C_4^- + 1\text{-}C_4^- \leftrightarrows C_2^- + 3\text{-}C_6^-$$

The metathesis reaction, in accordance with the invention may be effected at a temperature from about 50° C. to 600° C., preferably from about 200° C. to 350° C., at a weight hourly space velocity (WHSV) of from about 3 to about 200, preferably from about 6 to about 40, and at a pressure of from about 10 psig to about 600 psig, preferably from about 30 psig to about 100 psig.

The butene-1 starting material may be a pure or impure feed,. The portion of the feed that contains reactive $C_4$ olefins is preferably at least 90% and more preferably at least 95% butene-1. Non reactive components, for example normal butane, may dilute the olefins in the feedstock. Most preferably, the butene-1 starting material is a pure feed i.e. the butene-1 is present in an amount of at least 99%.

In one embodiment, a mixed butene feed is pretreated to provide a butene-1 feed for the metathesis reaction. For example, the mixed butene feed may contain butene-1, butene-2 and isobutylene. Such a feed may be obtained from a steam cracker In the event that the mixed butene stream includes butadiene such butadiene is removed by hydrogenation or extraction.

In one embodiment, the mixed butenes feed following or in conjunction with butadiene hydrogenation is subjected to hydroisomerization conditions to convert butene-1 to butene-2, with isobutylene being separated from a butene-2 stream by fractionation. The butene-2 stream is then isomerized back to butene-1 in a subsequent step for use as feed to the metathesis portion of the process The hydroisomerization of butene-1 to butene-2 and separation may be accomplished in separate steps or may be combined into a single step. In one embodiment butene-1 is isomerized to butene-2 and isobutylene is separated from butene-2, in a catalytic distillation tower In another embodiment, the isomerization of the butene-1 to butene-2 can also be accomplished by using a fixed bed isomerization reactor or by adjusting the conditions of the butadiene hydrogenation reactor followed by a fractionation tower to produce a butene-2 stream and an isobutylene product.

The isomerization of 1-butene to 2-butene is favored by low temperatures. This reaction is carried out typically in liquid phase either in a catalytic distillation tower or fixed bed reactor as described above.

The subsequent isomerization of 2-butene to 1-butene is favored by higher temperature and preferably is carried out in a vapor fixed bed phase reactor. Alternately, the conversion of butene-2 to butene-1 and the purification of the butene-1 may be accomplished by catalytic distillation. The production of 1-butene from hydrocarbons fed to a steam cracker is described further in U.S. Pat. No. 5,087,780, the contents of which are incorporated herein by reference.

As a further alternative, a mixed butene stream is reacted with for example methanol to convert isobutylene to methyl tertiary butyl ether (MTBE) as known in the art. The MTBE product is removed from the butenes stream. The resultant mixed normal butenes stream (butene-1 and butene-2) is then processed in a similar manner to the butene-2 stream above to produce an essentially pure butene-1 stream for feed to the metathesis reactor.

Thus, in accordance with an aspect of the present invention a mixed C4 stream is converted to ethylene and hexene-1 by the steps of a. hydrogenating the butadiene to 1 and 2 butenes, b. converting butene-1 to butene-2 and separating isobutylene therefrom, c. isomerization of butene-2 to produce butene-1, d. separation of butene 1 from butene 2 to produce an essentially pure butene 1 stream, e. autometathesis of butene-1 under non-isomerizing conditions to produce ethylene and hexene-3, and f. isomerizing hexene-3 to hexene-1.

The effluent from the metathesis reactor is passed to a series of fractionation towers, where ethylene is removed, unconverted butenes are separated for recycle, and the hexene fraction is removed from the bottoms. The bottoms stream, which is primarily 3-hexene, is isomerized to 1-hexene and the 1-hexene purified by fractionation. In a preferred embodiment, isomers of 2-hexene and 3 hexene are reacted essentially to extinction by recycle. The isomerization reaction schemes for hexene are essentially the same as described above for conversion of 2-butene to 1-butene. The overhead product is 1-hexene.

The hexene-3 produced in the autometathesis is isomerized in the presence of a suitable catalyst. The reaction can take place either in the liquid phase or the vapor phase. For liquid phase reaction, such catalysts include, but are not limited to, palladium and platinum catalysts. The catalyst may be supported on a suitable support material, such as alumina, for example. The reaction occurs in the presence of small amounts of hydrogen (hydroisomerization).

For vapor phase reaction, such catalysts include, but are not limited to, basic metal oxides, including magnesium oxide. In accordance with the invention, the metathesis reaction of the butene-1 occurs first, followed by the isomerization of the hexene-3 product from that reaction. In this case, no hydrogen is required. The equilibrium of mixed hexenes to 1-hexene is favored by higher temperatures hence the vapor phase reaction occurring at higher temperatures is preferred.

The hexene-3 may be isomerized to hexene-1 at a WHSV of from about 3 to about 200, preferably from about 10 to about 60, and at a pressure of from about 2 bar to about 40 bar, preferably from about 3 bar to about 10 bar, and a temperature from about 40° C. to 300° C., preferably from about 60° C. to 150° C. for liquid phase and 300 to 400 C for vapor phase reaction.

Although in accordance with the present invention, the metathesis reaction is effected with a catalyst and under conditions that minimize isomerization, some isomerization occurs. As a result of the isomerization, the internal olefin of carbon number n, such as butene-2, is produced which reacts with the feed linear alpha olefin of carbon number n, such as butene-1, to produce propylene and a non-selective linear internal olefin of carbon number 2n–3, such as pentene-2, via the reaction:

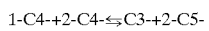

The propylene may be recovered as reaction product; however, in many cases, the internal olefin of carbon number 2n–3 is less valuable. In accordance with an aspect of the invention, pentene-2 is recycled to the metathesis reaction. The pentene-2 reacts with butene-1 to produce propylene and hexene-3 via the reaction:

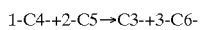

For example, in the metathesis of butene-1 under minimum isomerization conditions, there is about a 35 mol % selectivity of each of ethylene and hexene and 15 mol % of each of propylene and 2-pentene. This gives a 20% wt. selectivity to 2-$C_5H_{10}$. If the metathesis feed in addition to the 1-butene includes a stream of 2-pentene, such that the 2-pentene concentration in the feed is 10%, the net pentene selectivity goes to essentially 0 and the hexene selectivity increases from 35 to 46% molar or over 60% by weight. In this manner, hexene selectivity is increased.

In addition to participating in the above reaction, the presence of 2-pentene suppresses the formation of additional 2C5 by limiting the non-selective reaction of 1-butene with 2-butene due to equilibrium and ultimately limiting the isomerization of 1-butene to 2-butene because 2-butene formed is not reacting away, thus creating an additional equilibrium limitation.

In accordance with the present invention, the metathesis reaction of 1-butene is effected at conditions and with a catalyst that minimizes isomerization in order to increase selectivity to hexene-3 and ethylene. In particular, such catalyst and conditions are selected in order to achieve a weight selectivity to hexene-3 of at least 40% and preferably at least 50% or greater from l-butene (without recycle) and still higher values when incorporating pentene recyle.

The invention now will be described with respect to the following example; however, the scope of the present invention is not intended to be limited thereby.

EXAMPLE 1

In this example, a catalyst consisting of $WO_3$ on a silica support is loaded into a reactor either alone, or admixed with MgO prior to loading. Pure 1-butene is passed over the catalyst at a WHSV of 13 and at various pressures as shown in Table 1 below. The reaction temperature is 650° F. (343 C) over the catalyst. Selectivity is calculated by dividing the weight of each product by the weight loss of 1-butene converted to products. The selectivities to various components are given in Table 1 below.

TABLE 1

Weight percent Selectivity of 1-butene conversion to products

|  | 3/1 MgO/WO3 | | 1/1 MgO/WO3 | | Pure WO3 | Pure WO3 | Pure WO3 |
| --- | --- | --- | --- | --- | --- | --- | --- |
| Residence Time | 8 sec | | 12 sec | | 12 sec | 4 sec | 2 sec |
| Pressure | 275 psi | 275 psi | 450 psi | 450 psi | 450 psi | 150 psi | 75 psi |
| C2- | 2.5 | 2.5 | 2.1 | 2.4 | 13.9 | 17.8 | 17.4 |
| C3- | 26.3 | 22.9 | 23.3 | 23.9 | 14.9 | 9.2 | 9.1 |
| 2-C4- | 31.2 | 31.6 | 32.8 | 30.4 | 2.8 | 1.0 | 0.6 |
| 2-C5- | 19.2 | 18.1 | 24.8 | 25.0 | 16.9 | 11.0 | 11.2 |
| 1-C5- | 2.5 | 2.5 | 1.8 | 2.0 | 5.8 | 3.6 | 1.8 |
| C6 | 8.4 | 12.1 | 10.1 | 10.8 | 36.2 | 50.5 | 54.1 |
| C7 | 2.3 | 5.5 | 2.1 | 2.3 | 4.8 | 3.1 | 1.9 |
| C8+ | 3.7 | 5.5 | 1.0 | 1.0 | 2.0 | 1.3 | 3.9 |

As shown in Table 1 above, both the 3/1 and the 1/1 ratio mixtures of MgO and $WO_3$-$SiO_2$ catalyst show low weight selectivity to ethylene and $C_6$ alkenes. The isomerization activity of the MgO effectively converts some portion of the 1 butene to 2-butene and the metathesis reaction of:

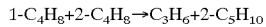

$$1\text{-}C_4H_8 + 2\text{-}C_4H_8 \rightarrow C_3H_6 + 2\text{-}C_5H_{10}$$

occurs limiting the auto-metathesis reaction of 1-$C_4H_8$ to form $C_2H_4 + 3$-$C_6H_{12}$.

When a pure $WO_3$-$SiO_2$ catalyst is employed, the selectivity for hexene increased from 8.4%–12.1% to as high as 54.1% hexene. The theoretical weight selectivities for the pure autometathesis reaction itself (no isomerization) are 25 wt. % ethylene and 75 wt. % hexene. Thus, reducing the isomerization activity of the catalyst system improved selectivity to hexene.

EXAMPLE 2

In this example, a feed containing pure 1-butene, and feeds containing 1-butene mixed with 2-butene or isobutylene are reacted in a reactor in the presence of a catalyst consisting of $WO_3$ and a silica support at a temperature of 600° F. or 650° F., and a pressure of 75 psig. These conditions and catalyst are preferred to minimize isomerization reactions. Selectivity is calculated in wt. % or mol. % by dividing the weight and number of moles of each product by the weight loss and molar loss of 1-butene converted to products. The selectivities to various components are given in Table 2 below.

TABLE 2

| | Feed (wt. %) | | |
| --- | --- | --- | --- |
| | A | B | C |
| 1-$C_4$ | 100 | 75 | 95 |
| 2-$C_4$ | 0 | 25 | 0 |
| i-$C_4$ | 0 | 0 | 5 |
| Temp. (° F.) | 650 | 600 | 600 |
| Pressure (psig) | 75 | 75 | 75 |
| Conversion (%) | | | |
| 1-$C_4$ | 47 | 52 | 56 |
| 2-$C_4$ | N/A | 66 | N/A |
| i-$C_4$ | N/A | N/A | 31 |
| Selectivity (mol %) | | | |
| $C_2H_4$ | 37 | 15 | 31 |
| 3-$C_6H_{12}$ | 38 | 19 | 28 |
| $C_3H_6$ | 12 | 34 | 19 |
| 2-$C_5H_{10}$ | 11 | 29 | 18 |
| Others | 2 | 3 | 4 |
| Selectivity (wt. %) | | | |
| $C_2H_4$ | 18.5 | 7.5 | 15.5 |
| 3-$C_6H_{12}$ | 57 | 28.5 | 42 |
| $C_3H_6$ | 9 | 25.5 | 14 |
| 2-$C_5H_{10}$ | 14 | 36.0 | 22.5 |
| Others | 1.5 | 2.5 | 6 |

The above results show that when the feed containing 1-butene is a feed of pure 1-butene with no other components, there is increased selectivity to 3-hexene, as compared with feeds containing 2-butene or isobutylene along with 1-butene.

EXAMPLE 3

In this example, a feed containing essentially pure 1-butene (95% 1-butene and 5% iso-butene) and a feed containing 1-butene, iso-butene and 10% 2-pentene are reacted in a reactor in the presence of a catalyst consisting of $WO_3$ and a silica support at a temperature of 650° F., and a pressure of 75 psig. These conditions and catalyst are preferred to minimize isomerization reactions. Selectivity is calculated in wt. % and mol. % by dividing the weight and number of moles of each product by the weight loss and molar loss of 1-butene converted to products. The selectivities to various components are given in Table 3 below.

TABLE 3

| | Feed (wt. %) | |
| --- | --- | --- |
| | A | B |
| 1-$C_4$ | 95 | 87 |
| I—$C_4$- | 5 | 3 |
| 2-$C_5$ | 0 | 10 |
| Temp. (° F.) | 650 | 650 |
| Pressure (psig) | 75 | 75 |
| Conversion (%) | | |
| 1-$C_4$ | 56 | 47 |
| 2-$C_5$ | N/A | 26 |
| i-$C_4$ | 31 | 29 |

TABLE 3-continued

| | Feed (wt. %) | |
|---|---|---|
| | A | B |
| Selectivity (mol %) | | |
| $C_2H_4$ | 31 | 34 |
| 3-$C_6H_{12}$ | 28 | 43 |
| $C_3H_6$ | 19 | 17 |
| 2-$C_5H_{10}$ | 18 | 1.6 |
| Others | 4 | 4.4 |
| Selectivity (wt. %) | | |
| $C_2H_4$ | 15.5 | 16.9 |
| 3-$C_6H_{12}$ | 42 | 64.1 |
| $C_3H_6$ | 14 | 12.7 |
| 2-$C_5H_{10}$ | 22.5 | 2.0 |
| Others | 6 | 4.3 |

The above results show that when the 2-pentene produced by the non-selective isomerization of the low isomerization catalyst is recycled, there is increased selectivity to 3-hexene, as compared with feed where the 2-pentene is not recycled to the reactor. If the base feedstock was a pure 1-butene stream, the increase in hexene selectivity would be even greater.

EXAMPLE 4

In this example, feeds containing essentially pure 1-butene (99.9% 1-butene), and feeds containing 1-butene and 2-pentene are reacted in a reactor in the presence of Catalyst A or Catalyst B at a temperature of 650° F. and a pressure of 75 psig. These conditions are preferred to minimize isomerization reactions. Catalyst A consists of $WO_3$ and a silica support, and Catalyst B consists of $WO_3$ and a special chromatographic grade silica support. Catalyst A uses a silica support that contains 2,000 ppm sulfur, thus creating acidic reaction sites. Catalyst B uses a silica support where the sulfur has been reduced to less than 100 ppm. Both catalysts have a low isomerization activity, and the isomerization activity of Catalyst B is lower than that of Catalyst A. Selectivity is calculated in wt. % and mol % by dividing the weight and number of moles of each product by the weight loss and molar loss of 1-butene converted to products. The selectivities to various components are given in Table 4 below.

TABLE 4

| | Feed (wt. %) | | | |
|---|---|---|---|---|
| Catalyst | A | A | B | B |
| 1-$C_4$ | 99.9 | 87.6 | 99.9 | 91.3 |
| 2-$C_5$ | 0 | 10.2 | 0 | 8.7 |
| Temp. (° F.) | 650 | 650 | 650 | 650 |
| Pressure (psig) | 75 | 75 | 75 | 75 |
| Conversion % | | | | |
| 1-$C_4$ | 56 | 45.4 | 41 | 38 |
| 2-$C_5$ | Net Production | 26.6 | Net Production | 32.5 |
| i-$C_4$ | N/A | 24.4 | N/A | N/A |
| Selectivity (mol %) | | | | |
| $C_2H_4$ | 31 | 35.5 | 44.2 | 38.4 |
| 3-$C_6H_{12}$ | 28 | 46.2 | 45.8 | 47.8 |
| $C_3H_6$ | 19 | 15.5 | 5.2 | 11.6 |
| 2-$C_5H_{10}$ | 18 | Net Conversion | 4.4 | Net Conversion |
| Others | 4 | 2.8 | 0.4 | 2.2 |
| Selectivity (wt. %) | | | | |
| $C_2H_4$ | 15.5 | 17.8 | 22.1 | 19.2 |
| 3-$C_6H_{12}$ | 42 | 69.3 | 68.6 | 71.7 |
| $C_3H_6$ | 14 | 11.6 | 3.8 | 8.7 |
| 2-$C_5H_{10}$ | 22.5 | Net Conversion | 5.3 | Net Conversion |
| Others | 6 | 1.3 | 0.2 | 0.4 |

As can be seen in Table 4 above, the recycling of pentenes increases hexene selectivity and provides for a reduced pentene make. In these tests, between 26 and 38% of the pentenes in the feed were converted when approximately 10% pentene was present in the feed. The selectivity increase is most significant when greater amounts of pentenes are produced. Note further, however, when using catalyst systems with high isomerization activity, the amounts of pentenes formed are so large as to render recycle impractical and very costly. This effect is most significant when using low isomerization activity catalysts.

The disclosures of all patents and publications (including published patent applications) are hereby incorporated by reference to the same extent as if each patent and publication were incorporated individually by reference.

It is to be understood, however, that the scope of the present invention is not to be limited to the specific embodiments described above. The invention may be practiced other than as particularly described and still be within the scope of the accompanying claims.

What is claimed is:

1. A process for producing ethylene and hexene-1 from a mixed $C_4$ feed containing butene-1, butene-2, butadiene, and isobutylene, comprising:
    (a) removing butadiene from said feed;
    (b) hydroisomerizing butene-1 to butene-2;
    (c) separating isobutylene from other butenes;
    (d) subsequent to said separation of isobutylene from other butenes, isomerizing butene-2 from step (b) to butene-1;
    (e) subjecting butene-1 from step (d) to catalytic metathesis under conditions and in the presence of a metathesis catalyst to produce a mixed olefin effluent including ethylene, pentene-2, and hexene-3, and wherein said pentene-2 is recycled to said butene-1 produced from step (d) to be subjected to catalytic metathesis;
    (f) fractionating the effluent; and
    (g) isomerizing hexene-3 from step (e) to produce hexene-1.

2. The process of claim 1 wherein steps (b) and (c) occur simultaneously in a catalytic distillation tower.

3. The process of claim 1 wherein said butene-1 is at least 90% of said feed.

4. The process of claim 1 wherein said catalyst is selected from the group consisting of tungsten oxide, molybdenum oxide, rhenium oxide, and mixtures thereof.

5. The process of claim 4 said catalyst does not include a promoter.

6. The process of claim 4 wherein said catalyst is tungsten oxide.

7. The process of claim 6 wherein said catalyst is supported tungsten oxide.

8. The process of claim 7 wherein said tungsten oxide is supported on a silica support.

9. The process of claim 1 wherein said hexene-3 is isomerized to hexene-1 at a WHSV of from about 3 to about 200.

10. The process of claim 9 wherein said hexene-3 is isomerized to hexene-1 at a WHSV of from about 10 to about 60.

11. The process of claim 1 wherein said hexene-3 is isomerized to hexene-1 at a pressure of from about 2 bar to about 40 bar.

12. The process of claim 11 wherein said hexene-3 is isomerized to hexene-1 at a pressure of from about 3 bar to about 10 bar.

13. The process of claim 1 wherein said metathesis in step (e) is effected at a temperature from 250° C. to 400° C.

14. The process of claim 1 wherein said hexene-3 is isomerized to produce hexene-1 at a temperature of from about 40° C. to about 400° C.

15. The process of claim 14 wherein said hexene-3 is isomerized to produce hexene-1 at a temperature of from about 250° C. to about 350° C.

16. A process for converting butene-1 to ethylene and hexene-1, comprising:
   (a) subjecting a feed comprised of at least 90% butene-1 to catalytic metathesis under conditions and with a metathesis catalyst that produces an effluent comprising ethylene and hexene-3 to provide a weight selectivity to hexene-3 of at least 40% from butene-1;
   (b) fractionating said effluent from step (a) into at least a first stream containing hexene-3 and a second stream including unreacted butene-1 and a pentene-2 olefin;
   (c) subjecting said first stream including said hexene-3 to isomerization to convert said hexene-3 to hexene-1;
   (d) subjecting said second stream of step (b) to metathesis by recycling said second stream to step (a); and
   (e) subjecting the combined effluent from the metathesis of said second stream and the metathesis of fresh feed in step (a) to fractionation in step (b).

17. The process of claim 16 wherein said weight selectivity to hexene-3 from butene-1 is at least 50%.

18. The process of claim 16 wherein said catalyst is selected from the group of tungsten oxide, molybdenum oxide, rhenium oxide, and mixtures thereof.

19. The process of claim 18 wherein said catalyst is tungsten oxide.

20. The process of claim 19 wherein said catalyst is supported tungsten oxide.

21. The process of claim 16 wherein the metathesis is effected at a WHSV of from about 3 to about 200.

22. The process of claim 21 wherein said metathesis is effected at a WHSV of from about 6 to about 40.

23. The process of claim 16 wherein said metathesis is effected at a pressure of from about 10 psig to about 600 psig.

24. The process of claim 23 wherein said metathesis is effected at a pressure of from about 30 psig to about 100 psig.

25. The process of claim 16 wherein said metathesis is effected at a temperature from 250° to 400° C.

26. The process of claim 19 wherein said catalyst is supported on a silica support.

27. The process of claim 16 wherein said hexene-3 is isomerized to hexene-1 at a WHSV of from about 3 to about 200.

28. The process of claim 27 wherein said hexene-3 to hexene-1 at a pressure of from about 2 bar to about 40 bar.

29. The process of claim 28 wherein said hexene-3 is isomerized to hexene-1 at a pressure of from about 3 bar to about 10 bar.

30. The process of claim 16 wherein said hexene-3 is isomerized to hexene-1 at a temperature of from about 40° C. to about 400° C.

31. The process of claim 30 wherein said hexene-3 is isomerized to hexene-1 at a temperature of from about 250° C. to about 350° C.

32. The process of claim 16 wherein said catalyst does not include a promoter.

* * * * *